United States Patent [19]

Jacobson et al.

[11] Patent Number: 5,310,916
[45] Date of Patent: May 10, 1994

[54] TRIFUNCTIONAL AGENTS USEFUL AS IRREVERSIBLE INHIBITORS OF A1-ADENOSINE RECEPTORS

[75] Inventors: Kenneth A. Jacobson, Silver Spring, Md.; Gary L. Stiles, Chapel Hill, N.C.; Daniel L. Boring, Rockville, Md.

[73] Assignee: The United States of America as represented by the Secretary of the Department of Health and Human Services, Washington, D.C.

[21] Appl. No.: 572,410

[22] Filed: Aug. 24, 1990

Related U.S. Application Data

[63] Continuation-in-part of Ser. No. 221,413, Jul. 19, 1988, abandoned.

[51] Int. Cl.$^5$ ............... C07D 331/00; A61K 31/52; A61K 31/505
[52] U.S. Cl. ............... 546/224; 546/244; 544/271; 544/272; 549/223; 549/225; 548/303.7; 548/304.1; 548/525; 548/542; 558/17
[58] Field of Search ............ 546/307, 308, 224, 244; 558/17; 549/388, 77, 224, 223, 225; 548/304.1

[56] References Cited

U.S. PATENT DOCUMENTS

| | | | |
|---|---|---|---|
| 3,480,424 | 11/1969 | Lemin et al. | 558/17 |
| 3,530,161 | 9/1970 | Hull et al. | 558/18 |
| 4,218,396 | 8/1980 | Hangwitz et al. | 558/17 |
| 4,820,709 | 4/1989 | Hofer | 514/263 |
| 4,879,296 | 11/1989 | Daluge et al. | 514/263 |

FOREIGN PATENT DOCUMENTS 326100 8/1989 European Pat. Off. .

OTHER PUBLICATIONS

Jacobson et al., J. Med. Chem. 32 1043-51, 1989.
Donaruma et al., Macromolecules 12(3) 435-38, 1979.
Jacobson, K. A. et al, *J. Med. Chem.*, 1985, 28:1334-40.
Jacobson, K. A. et al, *Proc. Natl. Acad. Sci. USA*, 1986, 83:4089-93.
Nakata, H. (1989) *J. Biol. Chem.*, vol. 264, 16545-16551.
Jacobson, K. A. et al, *Biochem. Pharmacol.*, 10:1697-1707 (1987).

*Primary Examiner*—Mukund J. Shah
*Assistant Examiner*—Matthew V. Grumbling
*Attorney, Agent, or Firm*—Leydig, Voit & Mayer Ltd.

[57] ABSTRACT

Trifunctional agents useful as inhibitors of $A_1$-Adenosine receptors may be formulated into pharmaceutical compositions. These agents are represented by formula (I):

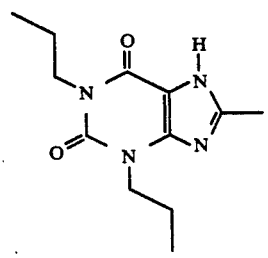

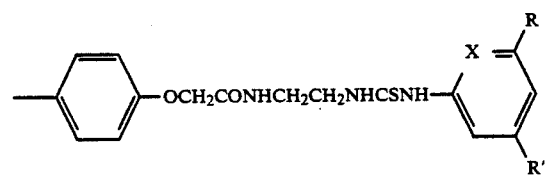

wherein X is CH or N, R is an isothiocyanate group, an amino group or $-NHCO_2C(CH_3)_3$ and $R^1$ is hydrogen, carboxyl, lower alkoxycarbonyl, aminocarbonyl,

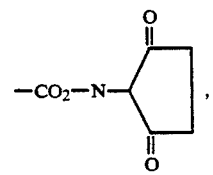

lower alkyl, optionally substituted with: $-OH$, (Abstract continued on next page.)

—COOH, lower ester of COOH, carboxamide, NHCOCH$_3$, NHCOCH$_2$Br, halo, dimethylamino, triethylammonium, NHCONH$_2$, SO$_2$NH$_2$, —SO$_3$H, or a reporter group, particularly a spectroscopic reporter group such as a fluorescent dye, photoaffinity probe, or spin label probe, coupled through an amide, sulfonamide, amine or thiourea linkage, biotinylamino- (optionally containing an ε-aminocaproyl spacer chain or similar spacer chain) or; R$^1$ is CONH—R$^2$ or NHCSNH—R$^2$, wherein R$^2$ is lower alkyl, optionally substituted with: —OH, —COOH, lower ester of COOH, carboxamide, NHCOCH$_3$, NHCOCH$_2$Br, halo, dimethylamino, triethylammonium, NHCONH$_2$, SO$_2$NH$_2$, —SO$_3$H, or a reporter group, particularly a spectroscopic reporter group such as a fluorescent dye, photoaffinity probe, or spin label probe, coupled through an amide, sulfonamide, amine, or thiourea linkage, biotinylamino- (optionally containing an ε-aminocaproyl spacer chain or similar spacer chain).

18 Claims, No Drawings

TRIFUNCTIONAL AGENTS USEFUL AS IRREVERSIBLE INHIBITORS OF A1-ADENOSINE RECEPTORS

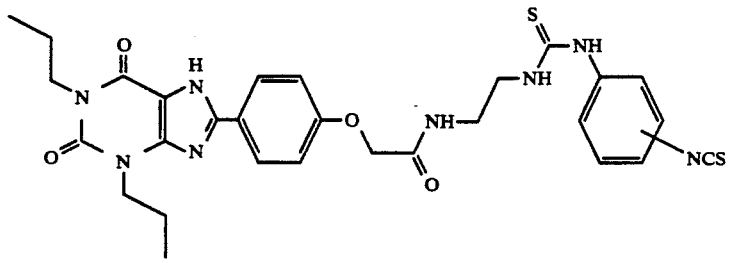

2a = meta-DITC-XAC
2b = para-DITC-XAC

This application is a continuation-in-part of application U.S. Ser. No. 07/221,413, filed Jul. 19, 1988, now abandoned, which is hereby fully incorporated herein by reference.

BACKGROUND OF THE INVENTION

1. Field of the Invention

The present invention relates to trifunctional agents useful as irreversible inhibitors of $A_1$-Adenosine receptors.

2. Description of Related Art

Adenosine acts as a neuromodulator at two receptor subtypes: $A_1$- and $A_2$-, which in general, inhibit or stimulate adenylate cyclase, respectively. Selective agonists and antagonists of each receptor subtype have been reported. The high affinity, $A_1$ selective antagonist 8-[4-[[[[(2-aminoethyl)-amino]carbonyl]methyl]oxy]phenyl]-1,3-dipropylxanthine (1), XAC, which has a $K_i$ value at rat brain $A_1$-receptors of 1.2 nM, was developed using a functionalized congener approach. Jacobson, K. A. et al, *J. Med. Chem.*, 1985, 28:1334-40.

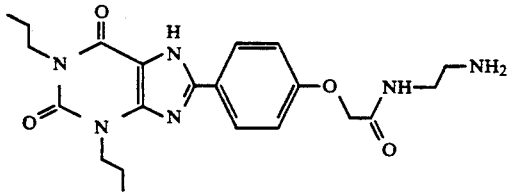

XAC has been useful in characterizing the $A_1$ receptor both as radioligand and as a ligand immobilized via its alkyl amino group for affinity chromatography of the receptor protein. Jacobson, K. A. et al, *Proc. Natl. Acad. Sci. USA*, 1986, 83:4089-93; Nakata, H. (1989) *J. Biol. Chem.*, 264, 16545-16551. The m- and p-phenylenediisothiocyanate conjugates of XAC (m-DITC-XAC (2a) and p-DITC-XAC (2b))), were prepared as high affinity, irreversible $A_1$ antagonists, with $K_i$ values at rat brain $A_1$-receptors of 2.4 and 6.6 nM, respectively.

These chemically reactive ligands have been used for identifying the $A_1$ receptor on electrophoretic gels and for blocking $A_1$-receptor mediated effects in physiological studies.

A general approach to systematically modifying the structure of irreversible ligand derivatives was desired to provide analogs. In previous studies of reversible ligands bearing spectroscopic labels, only moderate receptor affinities were attained, and this limited the utility of the ligands for histochemical studies. Jacobson, K. A. et al, *Biochem. Pharmacol.*, 10:1697-1707 (1987). A spectroscopic probe that binds irreversibly to the receptor would preclude problems of rapid washout and long equilibration times associated with reversible ligands. In addition, a difficulty encountered with 8-phenylxanthine derivatives in physiological studies is their typically low water solubility. Boykin, Dennis D. et al, *FASEB J.*, 4:A1008, Abstract 4306.

SUMMARY OF THE INVENTION

Therefore, it is an object of the present invention to provide trifunctional agents incorporating both chemically reactive groups (reactive towards ligands and/or receptors) and groups for changing the physical chemical properties or attaching reporter groups for receptor detection and characterization which exhibit improved receptor affinities.

It is another object of the present invention to provide trifunctional agents which allow for irreversible binding of a spectroscopic probe to a receptor.

It is a further object of the present invention to provide trifunctional agents which exhibit improved water solubility.

The foregoing objects and others are accomplished in accordance with the present invention by providing trifunctional agents of formula (I) as well as pharmaceutical compositions containing the same.

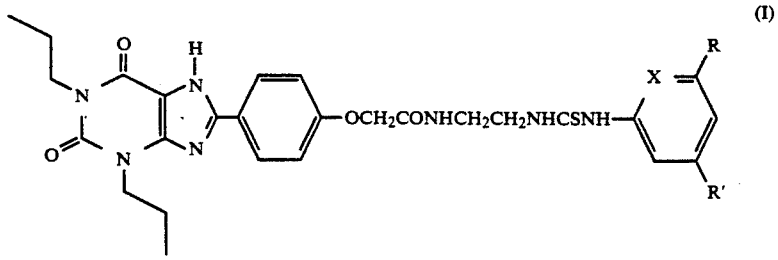

wherein X is CH or N, R is an isothiocyanate group, an amino group or —NHCO₂C(CH₃)₃ and R¹ is hydrogen, carboxyl, lower alkoxycarbonyl, aminocarbonyl,

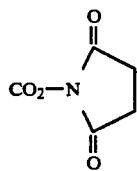

lower alkyl, optionally substituted with: —OH, —COOH, lower ester of COOH, carboxamide, NHCOCH$_3$, NHCOCH$_2$Br, halo, dimethylamino, triethylammonium, NHCONH$_2$, SO$_2$NH$_2$, —SO$_3$H, or a reporter group consisting of a spectroscopic reporter group, fluorescent dye, photoaffinity probe, or spin label probe, coupled through an amide, sulfonamide, amine or thiourea linkage, biotinylamino- (optionally containing an $\epsilon$-aminocaproyl spacer chain or similar spacer chain); or R$^1$ is CONH—R$^2$ or NHCSNH—R$^2$, wherein R$^2$ is lower alkyl, optionally substituted with: —OH, —COOH, lower ester of COOH, carboxamide, NHCOCH$_3$, NHCOCH$_2$Br, halo, dimethylamino, triethylammonium, NHCONH$_2$, SO$_2$NH$_2$, —SO$_3$H, or a reporter group consisting of a spectroscopic reporter group, fluorescent dye, photoaffinity probe, or spin label probe, coupled through an amide, sulfonamide, amine, or thiourea linkage, biotinylamino-(optionally containing an $\epsilon$-aminocaproyl spacer chain or similar spacer chain).

The present invention further encompasses intermediates useful in making the above trifunctional agents of the following formula (II):

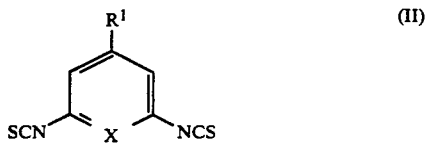

(II)

wherein X and R$^1$ are defined as indicated above with regard to formula (I).

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Scheme A presents an overview of the trifunctional strategy in which the trifunctional agents of the present invention are employed. An essential feature of this plan is the central linking unit, a 1,3,5-substituted benzene (3) that includes three reactive sites. These sites are 1) an acylating group for reaction with a functionalized congener, in this case the acylating group consists of an isothiocyanate group to react with XAC (affording general structure (4)); 2) another chemically reactive electrophilic group, such as an isothiocyanate, to combine irreversibly with the receptor protein and; 3) a site for incorporating a solubilizing or reporter moiety (group A in Scheme A). The symmetry of such a structure permits multiple synthetic pathways to a desired ligand. The m-diisothiocyanate structure was preserved in the synthetic design due to its proven merit in both attaching an amine-containing pharmacophore (XAC) and in acylating receptor residues. Jacobson, K. A. et al, J. Med. Chem., 32:1043–1051 (1989). The third feature, for solubility or spectroscopic characterization, could either be contained in a symmetrical diisothiocyanate intermediate to react with XAC or could be added to a reactive center already linked to the pharmacophore.

Scheme A

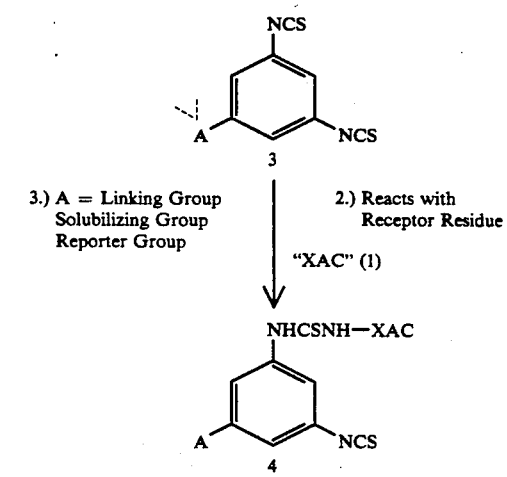

Previously, the feasibility of chemically crosslinking a functionalized congener, such as XAC or ADAC (N$^6$-[4-[[[4-[[[(2-Aminoethyl)amino]carbonyl]methyl]anilino]carbonyl]methyl]phenyl]adenosine), to a receptor by prior monovalent reaction of the ligand with a bifunctional reagent was demonstrated. Given the proximity to a nucleophile on the receptor, the remaining chemically reactive group of the congener was available for irreversible cross-linking during receptor binding. This approach afforded optimized irreversible ligands that proved useful in characterizing the A$_1$ receptor.

It became apparent from this earlier work that it would be desirable to incorporate additional substituents on the irreversible ligand for the purposes of altering physico-chemical and pharmacological properties. A number of possibilities can be envisioned involving prosthetic groups, reporter labels, additional reactive centers and water solubilizing moieties. One advantage of the present invention is the development of symmetrical trifunctional linkers and flexible synthetic methodologies which permit a diverse array of derivatives to be prepared.

In design consideration, it is important to maintain symmetry in the central linker in order to exercise a degree of regio-chemical control. This control could be achieved by having three equivalent reactive centers (such as the triisothiocyanatobenzene) and sequentially adding the necessary chemical components or by incorporating a desired modifying group at the outset then generating two equivalent reactive sites at a later stage of functionalization. The isothiocyanate group had proven to be an effective reactive site for the pharmacophore and receptor in previous work therefore at least two of the three sites in the linker were chosen to be isothiocyanates. Some variability of the linking moiety in the third site was needed to provide a logical means for attaching either a nucleophilic or electrophilic reagent for the desired chemical modification. For nucleophilic addition, the isothiocyanate group (leading to a thiourea) and N-hydroxysuccinimide active ester or acyl chloride (leading to a carboxamide) were chosen. To utilize the pool of commercially available amine reactive probes, a linker terminating in a free amine was also developed (compound x). This range of reaction tuning permits the permutability desired for different analogs.

The identification of irreversible inhibitors of adenosine receptors suggest studies in a number of physiological systems. For example, in the kidney both $A_1$ and $A_2$ receptors are present, and these receptors are not readily characterized in competitive binding studies, but might be differentiated with a ligand such as compound 10 identified below.

The central effects of adenosine (evidenced in locomotor depression, analgesia, protection against convulsions) had not been ascribed clearly to either $A_1$ or $A_2$ receptor subtypes. Recently however, the locomotor depression has been characterized pharmacologically as having both an $A_1$ and $A_2$ component. Addition of compound 10 as a specific inhibitor in isolated brain preparations or in vivo may prove to be a powerful tool for the study of regulatory effects of endogenous adenosine and delineation of the role of $A_1$ and $A_2$ receptor subtypes. It is possible that the metabolism of isothiocyanates in the liver and elsewhere will preclude the entry of purine isothiocyanate derivatives into the brain. If so, it will be necessary to administer the drug intracerebroventricularly for studies of the CNS.

The irreversible inhibitors of adenosine receptors have a therapeutic potential. In peripheral sites, a long acting adenosine antagonist (by virtue of covalent bond formation with the receptor) is of interest as a diuretic or kidney-protective agent, cardiotonic, or stimulator of the immune system. An irreversible adenosine agonist is of interest as a vasodilator, anti-diuretic agent, or immunosuppressant. In order that the trifunctional agents of the present invention may serve these purposes, the trifunctional agents may be incorporated into pharmaceutical compositions by combination with appropriate pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. The following methods and excipients are merely exemplary and are in no way limiting.

In pharmaceutical dosage forms, the trifunctional agents employed in the present invention may be used in the form of their pharmaceutically acceptable salts, and also may be used alone or in appropriate association, as well as in combination with other pharmaceutically active compounds.

In the case of oral preparations, the trifunctional agents may be used alone or in combination with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, the trifunctional agents employed in the present invention may be made into suppositories by mixing with a variety of bases such as emulsifying bases or water-soluble bases.

The trifunctional agents employed in the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the trifunctional agents employed in the invention in the form of a liquid or minute powder may be filled up in an aerosol container with gas or liquid spraying agents, and if desired, together with conventional adjuvants such as humidifying agents. They may also be formulated as pharmaceuticals for non-pressured preparations such as in a nebulizer or an atomizer.

The amount of the trifunctional agents employed in the present invention to be used varies according to the degree of the infection encountered, and the stages of the disease. A suitable dosage is that which will result in concentration of the trifunctional agent in blood and/or target tissues of about 10 $\mu$g/kg body weight to 10 mg/kg body weight. The preferred dosage is that amount sufficient to render a host asymptomatic. The dose may vary when the compounds are used prophylactically.

Unit dosage forms for oral administration such as syrups, elixirs, and suspensions wherein each dosage unit, e.g., teaspoonful, tablespoonful, contains a predetermined amount of the trufunctional agents employed in the present invention can be by a pharmaceutically acceptable carrier, such as Sterile Water for Injection, USP, or by normal saline.

The trifunctional agents employed in the present invention can be utilized in aerosol formulation to be administered via inhalation. The trifunctional agents employed in the present invention can be formulated into pressurized acceptable propellants such as dichlorodifluoromethane, propane, nitrogen and the like.

The term "unit dosage form" as used herein refers to physically discrete units suitable a unitary dosages for human and animal subjects, each unit containing a predetermined quantity of the trifunctional agents calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, for example, vehicles, adjuvants, carriers or diluents are readily available to the public.

Any necessary adjustments in dose can be readily made to meet the severity of the infection and adjusted accordingly by the skilled practitioner.

EXAMPLES

Table 1 lists the xanthine analogs synthesized, including derivatives having photoreactive (18), fluorescent (e.g. 21, 22, 26 and 27), spin label (20), fluorinatable (28)

or iodinatable (17) reporter groups or solubilizing (e.g. 9, 10, 13–16, 24, 25) groups.
TABLE 1
Synthesis and characterization of xanthine derivatives.
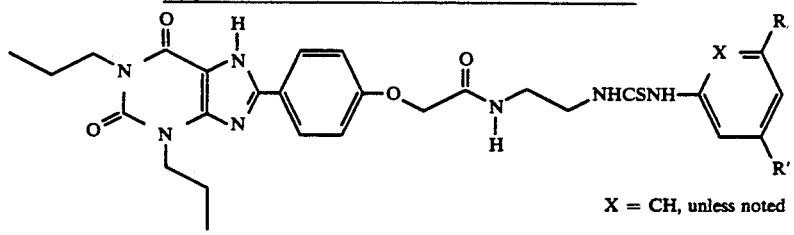
X = CH, unless noted
| Compound | R = | R' = |
|---|---|---|
| 5 | NH$_2$ | H |
| 6 | NHCO$_2$C(CH$_3$)$_3$ | H |
| 7 | NCS | H |
| 8 | NCS (X = N) | H |
| 9 | NCS | CH$_2$OH |
| 10 | NCS | COOH |
| 11 | NCS | COOC$_2$H$_5$ |
| 12 | NCS | 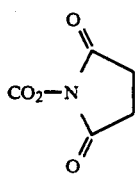 |
| 13 | NCS | CONH$_2$ |
| 14 | NCS | CONH(CH$_2$)$_2$N(CH$_3$)$_2$ |
| 15 | NCS | CONH(CH$_2$)$_2$N(CH$_3$)$_3$Cl |
| 16 | NCS | CONH(CH$_2$)$_2$NHCOCH$_3$ |
| 17 | NCS | 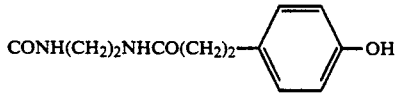 |
| 18 | NCS | 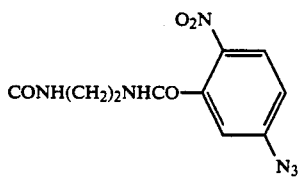 |
| 19 | NCS | 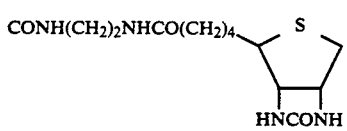 |
| 20 | NCS | 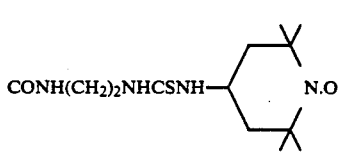 |
| 21 | NCS | 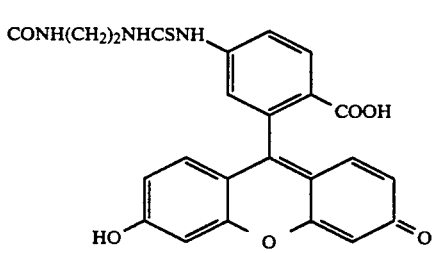 |

TABLE 1-continued

Synthesis and characterization of xanthine derivatives.

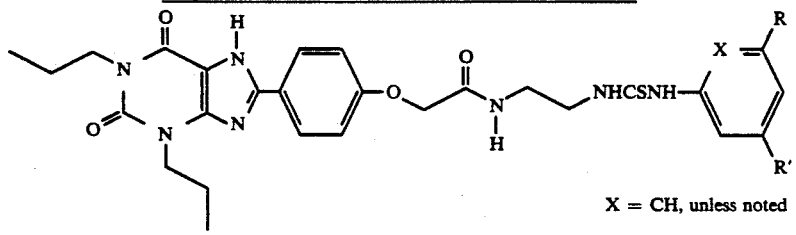

X = CH, unless noted

| Compound | R = | R' = |
|---|---|---|
| 22 | NCS | CONH(CH₂)₂NHCSNH—[fluorescein-like dye structure with (CH₃)₂N, COOH, N(CH₃)₂·Cl] |
| 23 | NCS | NCS |
| 24 | NCS | NHCSNH(CH₂)₂N(CH₃)₂ |
| 25 | NCS | NHCSNH(CH₂)₂NHCOCH₃ |
| 26 | NCS | NHCSNH(CH₂)₂NHCSNH—[fluorescein structure with HO, COOH, =O] |
| 27 | NCS | NHCSNH(CH₂)₂NHCSNH—[rhodamine structure with (CH₃)₂N, COOH, N(CH₃)₂·Cl] |
| 28 | NCS | NHCSNH(CH₂)₄NHCO—[phenyl-CH₂Br] |

Chemistry

A. Diisothiocyanates. All of the m-diisothiocyanate intermediates within the general formula of Scheme A as listed in Table 2 were prepared either by treatment of their penultimate m-diamines with thiophosgene in the presence of base or by addition of a primary amine to 1,3,5-triisothiocyanatobenzene in general accordance with the procedures indicated in Jacobson, K. A. et al, *J. Med. Chem.*, 32:1043-1051 (1989). These diamines were derived from m-phenylenediamines, m-di-t butoxycarbonylamino or m-dinitro compounds. Two different reactive units were chosen for group A in Scheme A, consisting of either an isothiocyanate to afford an N-substituted thiourea or an activated acyl to give a carboxamide. The thiourea intermediates were prepared by addition of a primary amine to 1,3,5-triisothiocyanatobenzene (isothiocyanic acid, s-phenenyl triester) whereas the carboxamides arose from 3,5-diaminobenzoic acid.

TABLE 2
Synthesis of isothiocyanate intermediates.

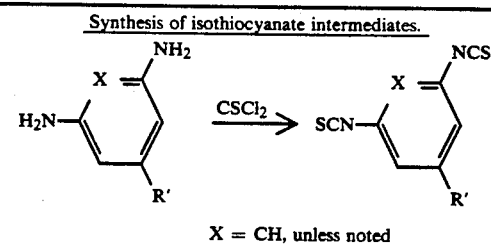

X = CH, unless noted

| Compound | R' = |
|---|---|
| 29 | X = N<br>R' = H |
| 30 | CO$_2$H |
| 31 | CO$_2$Et |
| 32 | CH$_2$OH |
| 33 | CONH(CH$_2$)$_2$N(CH$_3$)$_2$ |
| 34 | CONH(CH$_2$)$_2$NHAc |
| 35 | CONH$_2$ |
| 37 | NHCSNH(CH$_2$)$_2$N(CH$_3$)$_2$ |
| 38 | NHCSNH(CH$_2$)$_2$NHAc |

39 CONH(CH$_2$)$_2$NHCO(CH$_2$)$_2$—⟨C$_6$H$_4$⟩—OH

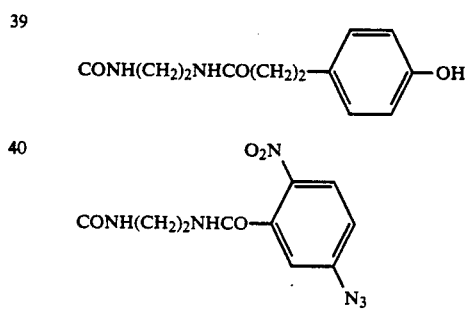

40 CONH(CH$_2$)$_2$NHCO—[2-O$_2$N, 5-N$_3$ phenyl]

41 CONH(CH$_2$)$_2$NHCO(CH$_2$)$_4$—[thiolane with HNCONH]

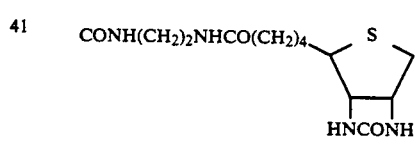

42 CONH(CH$_2$)$_2$NHCSNH—[TMP-N.O]

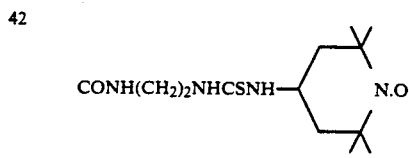

TABLE 2-continued
Synthesis of isothiocyanate intermediates.

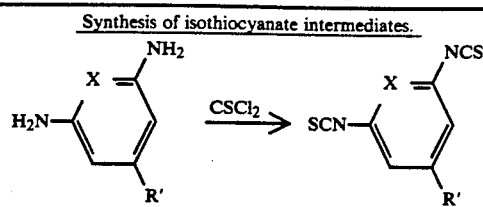

X = CH, unless noted

| Compound | R' = |
|---|---|
| 43 | CONH(CH$_2$)$_2$NHCSNH— (fluorescein derivative) |

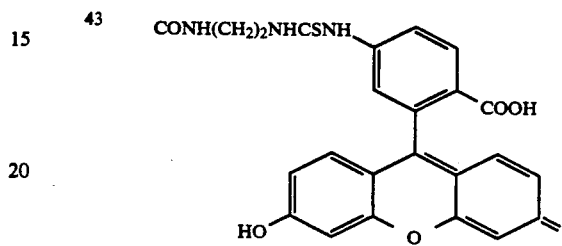

Scheme I shows a representative example of the conditions used to prepare the diisothiocyanates. The diamino ester 44 was also used to prepare alcohol 32 by first reducing the ester to the corresponding diamino alcohol 45, then converting the diamino alcohol to the diisothiocyanate as shown in Scheme I. The pyridine diisothiocyanate 29 was included in hope that the annular heteroatom would afford some degree of solubization or altered receptor subtype selectivity.

Scheme I.

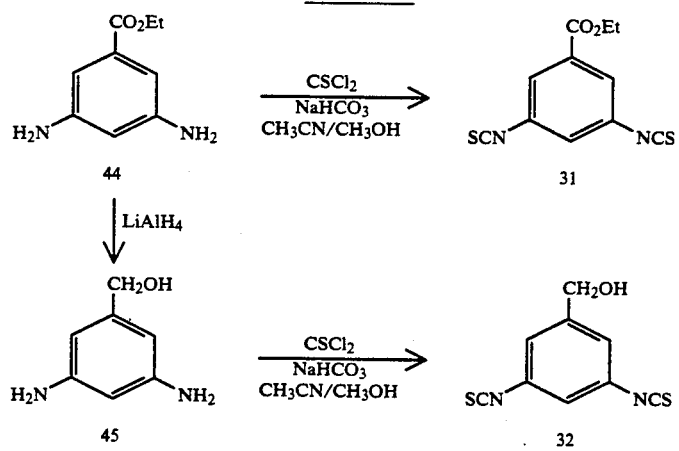

Dinitro precursor compounds, derived from 3,5-dinitrobenzoyl chloride, were reduced to their diamino structures by catalytic hydrogenation using 10% Pd/C as illustrated in Scheme II for the conversion of the dinitro amides 46a,b into the diamino amides 47a,b. The diamino intermediates were not isolated, but used directly for the diisothiocyanate formation, then purified. The diamino carboxamides were subsequently converted to diisothiocyanates 33 and 34 by the usual method. The same sequence was used to prepare compounds 36 from 3,5-dinitrobenzamide and 35 from 3,5-dinitroaniline.

Scheme II.

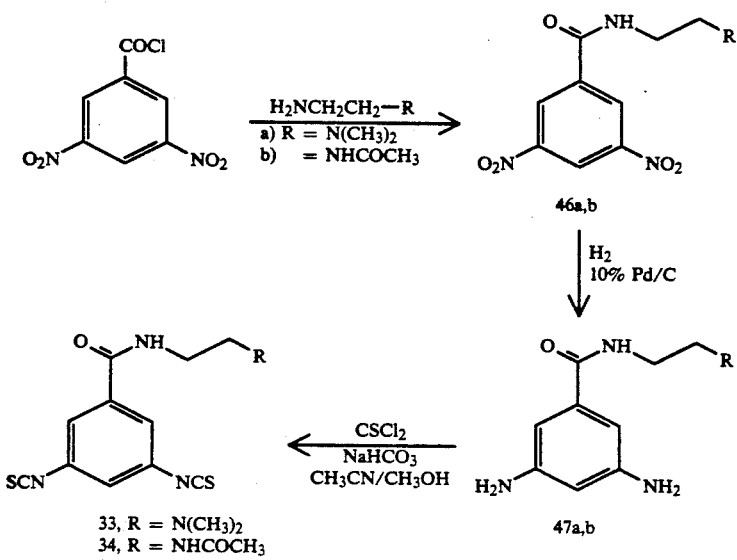

The thiourea diisothiocyanates 37 and 38 were prepared by the reaction of excess 1,3,5-triisothiocyanatobenzene with N,N-dimethylethylenediamine or N-acetylethylenediamine in dimethoxyethane as presented in Scheme III.

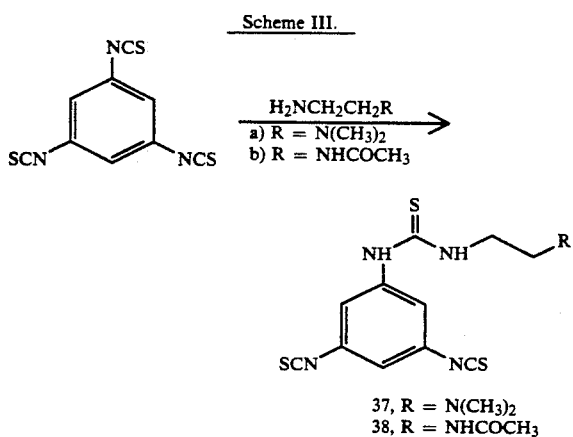

Scheme IV illustrates another general route to the diisothiocyanates beginning with 3,5-diaminobenzoic acid. With the two amino groups protected as t-butylcarbamates (Boc), the acid is esterified in methanol using ethyldimethylaminopropylcarbodiimide (EDAC) and 4-dimethylaminopyridine, followed by aminolysis with ethylenediamine, to give 48. This was condensed with chemically reactive reporter precursors. The Boc groups were removed by trifluoroacetic acid affording diamines, which were converted to the diisothiocyanates 39–43 by the usual method. Alternatively, the di-Boc protected 3,5-diaminobenzoic acid may be converted to its hydroxysuccinimide active ester xx, which can be conveniently coupled to an amine bearing probe (such as 5-((2-aminoethyl)thioureidyl)fluorescein) then deprotected and transformed into the corresponding diisothiocyanate in the aforementioned manner (Scheme V).

Scheme IV.

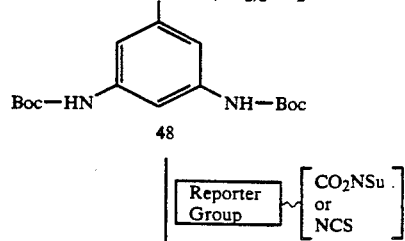

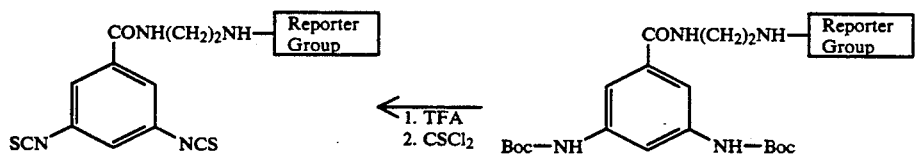
Scheme V.
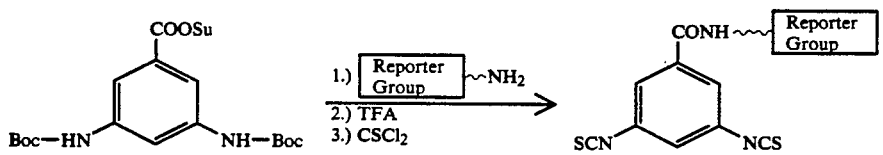
A summary for the overall synthesis strategy used to make the compounds of the present invention is provided in Schemes VI and VII below.
Scheme VI
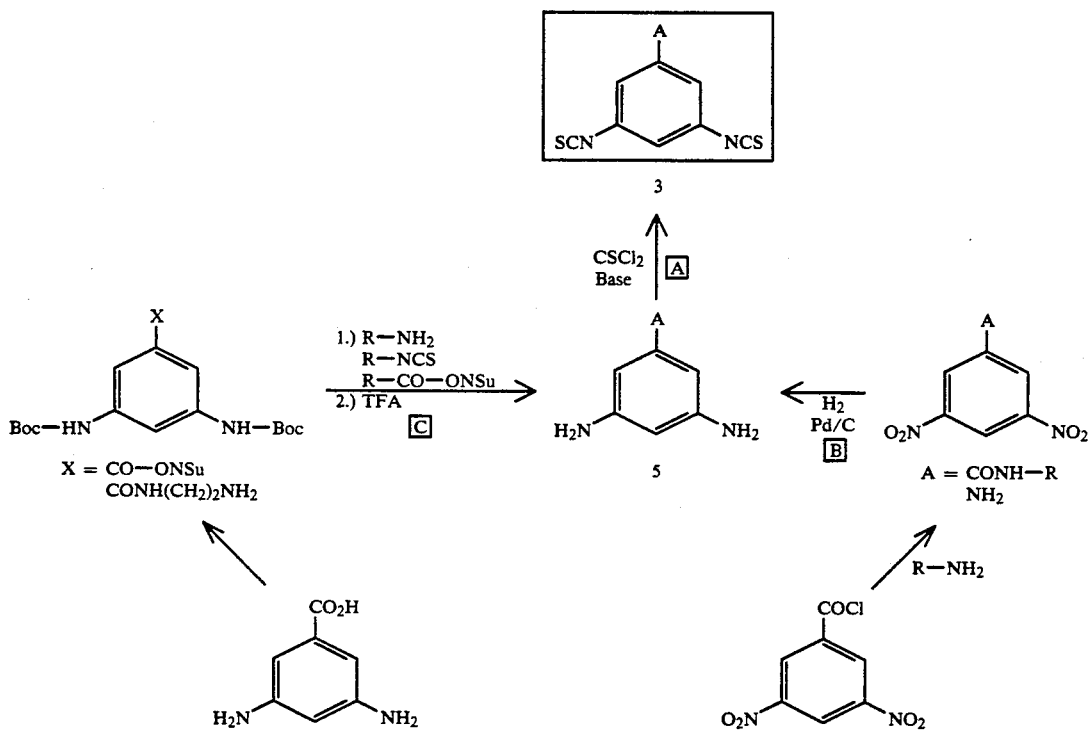
Scheme VII
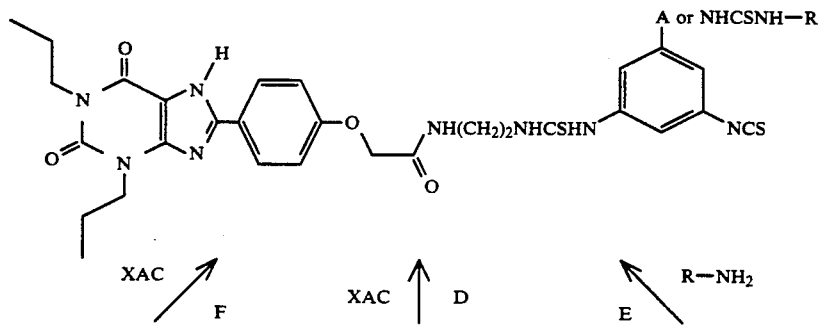

Scheme VII

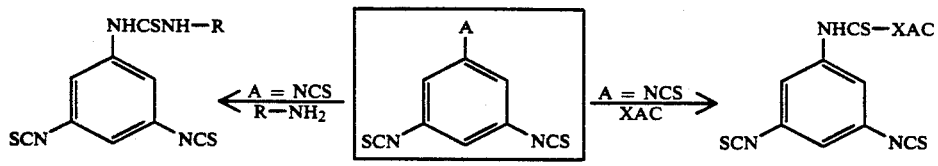

B. Diisothiocyanate/XAC Conjugates.

All of the XAC conjugates were prepared by coupling of an excess of the necessary diisothiocyanate with XAC in DMF using sonication to effect solubilization. The product was then precipitated by addition of either diethyl ether or ethyl acetate (Scheme A).

C. Additional Derivatives

Solubility of Analogs

The method for determining the solubilities of the xanthines is detailed in the Experimental Section below. The solubility (in uM) of selected derivatives is presented in Table 3.

TABLE 3

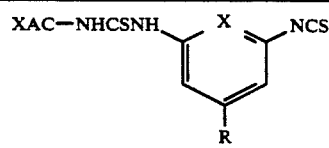

| Compound | | Solubility (uM) |
|---|---|---|
| X = N, R = H | | 17.5 ± 0.06 |
| All the following X = CH | | |
| | R = H | 90.1 ± 0.56 |
| 11 | R = CO₂Et | 9.33 ± 0.43 |
| 13 | R = CONH₂ | 31.4 ± 0.39 |
| 9 | R = CH₂OH | 10.8 ± 0.03 |
| 14 | R = CONHCH₂CH₂N(CH₃)₂ | 28.7 ± 0.03 |
| 16 | R = CONHCH₂CH₂NHAc | >1000 |
| 25 | R = NHCSNHCH₂CH₂NHAc | >100 |

Biology

The $K_i$ values (in nM) for $A_1$ and $A_2$ binding in rat striatum are presented in Table 4 with the relative selectivities expressed as the ratio of $K_i$ values. The most potent and selective of the potentially irreversibly binding xanthines were the sixth, eleventh, fouteenth, and seventeenth listed compounds listed in Table 4. Table 4 also indicates the synthesis method used for each compound therein.

TABLE 4

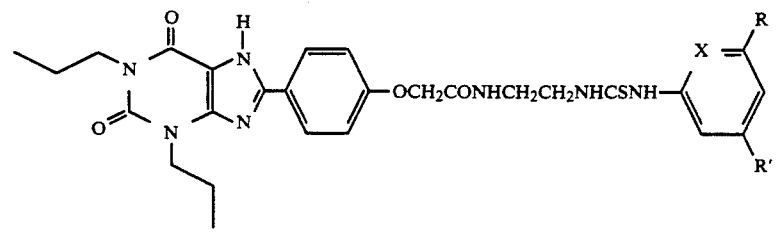

| | $K_i$ at central rat receptors, nM | | | |
|---|---|---|---|---|
| compd. and structure | $A_1$ | $A_2$ | $A_2/A_1$ ratio | Method |
| X = N, R = NCS, R' = H | 16.2 ± 1.96 | 432 ± 20 | 27 | A,D |
| X = CH, R = NCS in all following: | | | | |
| R' = H (m-DITC-XAC) | 2.39 ± 0.35 | 343 | 144 | A,D |
| R' = CO₂Et | 41.6 ± 8.2 | 815 ± 145 | 19 | A,D |
| R' = CH₂OH | 13.4 ± 2.64 | 433 ± 45 | 32 | A,D |
| R' = CONH₂ | 9.47 ± 2.99 | 365 ± 35 | 39 | B,D |
| R' = NCS | 3.96 ± 0.59 | 3541 ± 936 | 894 | B,D |
| R' = CONHCH₂CH₂N(CH₃)₂·HCl | 7.62 ± 2.19 | 497 ± 74 | 65 | B,D |
| R' = CONHCH₂CH₂NHAc | 7.01 ± 0.52 | 247 ± 36 | 35 | B,D |
| R' = NHCSNHCH₂CH₂N(CH₃)₂ | 77.2 ± 2.5 | 1914 ± 303 | 25 | F |
| R' = NHCSNHCH₂CH₂NHAc | 57.6 ± 15.7 | 2542 ± 283 | 44 | F |
| R' = NHCSNHCH₂CO₂t-Bu | 8.30 ± 2.20 | 3293 | 397 | F |
| R' = CONH(CH₂)₂NHCOCH₂Br | 15.8 | 688 | 44 | C,D |

TABLE 4-continued

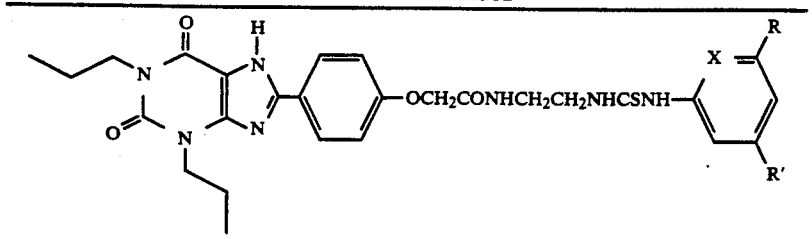

| compd. and structure | $K_i$ at central rat receptors, nM | | | |
|---|---|---|---|---|
| | $A_1$ | $A_2$ | $A_2/A_1$ ratio | Method |
| R' = 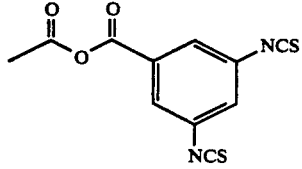 | 45.0 ± 3.5 | 493 ± 200 | 11 | A |
| R' = CONH(CH$_2$)$_2$NHCO(CH$_2$)$_2$ p-phenol | 7.08 ± 1.91 | 1404 | 198 | C,D |
| R' = NHCSNH(CH$_2$)$_2$NH-2-nitro-4-azido-benzene | 27.3 ± 7.2 | 842 | 31 | E |
| R' = NHCSNH(CH$_2$)$_2$NHCO-2-hydroxy-4-azidobenzene | 25.2 | 341 | 14 | E |
| R' = CONH(CH$_2$)$_2$NHCO-biotin | 20.1 ± 3.3 | 11,500 | 572 | C,D |
| R' = NHCSNH(CH$_2$)$_2$NHCSNH-TEMPO | 52.1 ± 16.4 | 435 | 8 | E |
| R' = NHCSNH(CH$_2$)$_2$NHCSNH-fluorescein | 234.0 ± 32.5 | 1791 | 8 | E |
| R' = NHCSNH(CH$_2$)$_4$NHCO-4-fluoromethylbenzene | 43.6 ± 12.3 | 595 | 14 | E |
| R' = CONH(CH$_2$)$_2$NH-NBD | 18.1 | 1327 | 73 | C,D |

$A_1$ ligand = [$^3$H]R-PIA, $A_2$ ligand = [$^3$H]CGS-21680
TEMPO = 2,2,6,6-tetramethyl-1-piperidinyloxy, NBD = 4-nitrobenz-2-oxa-1,3-diazole The degree of irreversible binding was determined as previously described and the percent inhibition of selected compounds is presented in Table 5.

TABLE 5

Percent Inhibition of $^{125}$I APNEA Binding (Irreversible Binding)

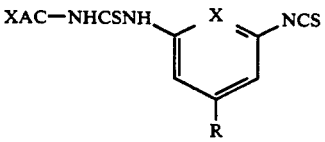

| Compound | Concentration (nM) | % Decrease |
|---|---|---|
| X = CH | | |
| 13, R = CONH$_2$ | 20 | 90.3 ± 7.0 |
| | 5 | 68.0 ± 7.5 |
| 14, R = CONHCH$_2$CH$_2$N(CH$_3$)$_2$ | 50 | 46.3 ± 21.8 |
| | 20 | 30.0 ± 8.7 |

Experimental Section

General. New compounds were characterized (and resonances assigned) by 300 MHz proton nuclear magnetic resonance spectroscopy using a Varian XL-300 FT-NMR spectrometer. Unless noted, chemical shifts are expressed as ppm downfield from tetramethylsilanae. Synthetic intermediates were characterized by $^1$H-NMR and by chemical ionization mass spectroscopy (CIMS, NH$_3$) using a Ginigan 1015 mass spectrometer modified with EXTREL electronics of on a Finnigan 4500 MS. Melting points were determined on a Thomas Hoover melting point apparatus and are uncorrected. C, H, and N was carried out by Atlantic Microlabs (±0.4% acceptable). The Chromatotron is a radially accelerated thin layer chromatography device manufactured by Harrison Research, Palo Alto, Calif. The following abbreviations are used EtOAc: ethyl acetate, DME: 1,2-dimethoxyethane, XAC: xanthine amine congener (1). [$^3$H]N$^6$-Phenylisopropyladenosine and [$^3$H]5'-N-ethylcarboxamidoadenosine were from Dupont NEN Products, Boston, Mass. N$^6$-Cyclopentyladenosine, XAC, and ADAC were obtained from Research Biochemicals, Inc., Natick, Mass.

General Method for coupling XAC with Diisothiocyanates. In 0.5 ml of dimethylformamide was placed 25 mg (58.4M) of XAC and a 3 molar excess of the requisite diisothiocyanate. This was sonicated for 3-5 min, during which time complete solution occurred. The reaction was monitored by HPLC for disappearance of XAC and was complete within 5 min. To the solution was added either EtOAc of Et$_2$O to precipitate the product. This precipitate was collected by centrifugation and was washed 3 times with fresh solvent for purification. The solid material was then dried overnight under vacuum at 50° C. The following compounds were prepared.

1,3-Dipropyl-8-(4-(((((2-((((3,5-diisothiocyanatophenyl)amino)thiocarbonyl)amino)ethyl)amino)carbonyl)methyl)oxy)phenyl)-xanthine.

1,3-Dipropyl-8-(4-(((((2-((((3-carboxy-5-isothiocyanatophenyl)amino)thiocarbonyl)amino)ethyl)amino)carbonyl)methyl)oxy)phenyl)xanthine.

1,3-Dipropyl-8-(4-(((((2-((((3-carbethoxy-5-isothiocyanatophenyl)amino)thiocarbonyl)amino)ethyl)amino)carbonyl)methyl)oxyl)phenyl)xanthine.

1,3-Dipropyl-8-(4-(((((2-((((3-hydroxymethyl-5-isothiocyanatophenyl)amino)thiocarbonyl)amino)ethyl)amino)carbonyl)methyl)oxyl)phenyl)xanthine.

1,3-Dipropyl-8-(4-(((((2-((((3-carboxamide-5-isothiocyanatophenyl)amino)thiocarbonyl)amino)ethyl)amino)carbonyl)methyl)oxy)phenyl)xanthine.

1,3-Dipropyl-8-(4-(((((2-((((6-isothiocyanatopyrido)amino)thiocarbonyl)amino)ethyl)amino)carbonyl)methyl)oxy)phenyl)xanthine.

1,3-Dipropyl-8-(4(((((2-((((3-aminophenyl)amino)thiocarbonyl)amino)ethyl)amino)carbonyl)methyl)oxy)-phenyl)xanthine.

1,3-Dipropyl-8-(4-(((((2-((((3-t-butoxycarbonylaminophenyl)amino)thiocarbonyl)amino)ethyl)amino)carbonyl)methyl)oxyl)phenyl)xanthine.

1,3-Dipropyl-8-(4-(((((-2-((((3-hydroxysuccinimidylcarboxy-5-isothiocyanatophenyl)amino)thiocarbonyl)amino)ethyl)amino)carbonyl)methyl)oxy)phenyl)xanthine.

1,3-Dipropyl-8-(4-(((((2-((((3-(2-dimethylaminoethylcarboxamide)-5-isothiocyanatophenyl)amino)thiocarbonyl)amino)ethyl)amino)carbonyl)methyl)oxy)-phenyl)xanthine.

1,3-Dipropyl-8-(4-(((((2-((((3-(2-acetylaminoethylcarboxamide)-5-isothiocyanatophenyl)amino)thiocarbonyl)amino)ethyl)amino)carbonyl)methyl)oxy)-phenyl)xanthine.

1,3-Dipropyl-8-(4-(((((2-(((((3-(((((2-dimethylamino)ethyl)amino)thiocarbonyl)amino)-5-isothiocyanatophenyl)amino)thiocarbonyl)amino)ethyl)amino)carbonyl)methyl)oxy)phenyl)xanthine.

1,3-Dipropyl-8-(4-(((((2-(((((3-(((((2-acetylamino)ethyl)amino)thiocarbonyl)amino)-5-isothiocyanatophenyl)amino)thiocarbonyl)amino)ethyl)amino)carbonyl)methyl)oxy)phenyl)xanthine.

General Methods for the preparation of diisothiocyanates

Method A. The diisothiocyanates prepared in this section were derived from the commercially available aromatic diamines as listed at the beginning of each entry. To a solution of 10 mM of the diamine dissolved in 50 ml of a 1:1 mixture of EtOH: CH3CN, containing 4 g (excess)of NaHCO3, cooled to 0° C. by ice/MeOH, was added 1.5 ml (excess) of thiophosgene all at once via syringe. This was allowed to warm to room temperature over a 1 h period, then quenched by the cautious addition of 100 ml of pH 4 NaH2PO4. The mixture was extracted three times with 100 ml portions of EtOAc. The extracts were combined and dried over anhyd Na2SO4, filtered and solvent removed by rotary evaporator. Final purification was effected by the Chromatotron using EtOAc: petroleum ether (1:4) as eluent.

2,6-Diisothiocyanatopyridine
Ethyl 3-5,diisothiocyanatobenzoate
3,5-Diisothiocyanatobenzyl alcohol Method B.

The following procedure was employed in those cases where the necessary aromatic diamine was prepared from its dinitro precursor. The diamines were not isolated, but were used in situ to prepare the desired diisothiocyanate. Into a hydrogenation bomb was placed 10 mM of the listed, commercially available, dinitro compound, 100 mg of 10% Pd on carbon as catalyst and 50 ml of MeOH as solvent. This was put into a Parr hydrogenator and shaken at room temperature under 25 psi of H2 for 2 h. TLC was used to determine reaction completion. When finished, the solution was filtered through a plug or Celite to remove catalyst and the methanolic solution of diamine treated directly to the conditions of Method A (presuming complete reduction) to prepare the desired diisothiocyanate. Final purification was effected by the Chromatotron using EtOAc: petroleum ether (1:4) as eluent.

3,5-Diisothiocyanatobenzamide
3,5-Diisothiocyanatobenzonitrile
1,3,5-Triisothiocyanatobenzene Method C.

The preparation of diisothiocyanates a-x was accomplished as follows. To a stirring solution of 20 mM of either N-acetylethylenediamine or N,N-dimethylethylenediamine (depending on the desired derivative) and excess triethylamine contained in 100 ml of DME at room temperature was slowly added 20 mM of 3,5-dinitrobenzoyl chloride in 20 ml of DME. A thick precipitate formed and the mixture was allowed to stir overnight whereupon 150 ml of 10% aqueous NaOH was added. The resulting mixture was extracted with 2×300 ml portions of EtOAc and the combined extracts washed sequentially with 0.5N HCl and brine. The organic fraction was separated, dried over anhyd Na2SO4, then solvent removed by rotary evaporator. The unpurified dinitro amide was then subjected to the conditions of Method B to yield the corresponding diamine, then to Method A to ultimately yield the listed diisothiocyanates. Final purification was either by Chromatotron using EtOAc: petroleum ether (1:4) or by recrystallization.

N-(2-Acetylaminoethyl)-3,5-diisothiocyanatobenzamide

N-(2-Dimethylaminoethyl)-3,5-diisothiocyanatobenzamide

Method D.

The following procedure was used to prepare diisothiocyanates a-x. To 500 mg (2 mmol) of triisothiocyanato benzene contained in 50 ml of DME, cooled to 0° C. by ice/MeOH was added 0.66 mmol of either N-acetylethylenediamine of N,N-dimethylethylenediamine (depending on the desired derivative). This was stirred in the cold for 1 h, then solvent removed by the rotary evaporator. The remaining residue was placed on the Chromatotron with the initial eluent being EtOAc: petroleum ether (1:4) until the first band (triisocyanatobenzene) was removed, then replaced by pure EtOAc until the second band (the desired product) was collected.

N-(3,5-Diisothiocyanatophenyl)N'-(2-acetylaminoethyl)-thiourea

N-(3,5-Diisothiocyanatophenyl)N'-(2-dimethylaminoethyl)-thiourea

Method E.

3,5-Di-(t-butyloxycarbonylamino)benzoic acid 3,5-Diaminobenzoic acid dihydrochloride (10 g, 44 mmol) was added to 120 ml of 1M aqueous sodium hydroxide. Methanol (60 ml) was added. Di-t-butyldicarbonate (19 g, 87 mmol) dissolved in 15 ml methanol was added to the diamine with stirring. After 12 hours, the reaction was acidified with citric acid and extracted with ethyl acetate. The organic layer was dried (Na2SO4) and evaporated. Addition of ether resulted in the precipitation of salts, which were removed by filtration. The ether solution was extracted with cold 1N HCl. After separation, the organic solvent was evaporated in vacuo leaving a white solid. Yield 9.65 g (62%), mp. 113–116.

Methyl 3,5-di-(t-butyloxycarbonylamino)benzoate 3,5-Di-(t-butyloxycarbonylamino)benzoic acid (5.00 g, 14.2 mmol) was esterified in methanol using ethyldimethylaminopropylcarbodiimide (14.2 mmol) and dimethylaminopyridine (2.4 mmol). After 2 hours the product precipitated as a solid and was collected, washed with a small amount of methanol, and dried in vacuo. A second crop was collected yielding a total of 3.64 g (70%) of product. Mp. 206–207.

2-[3,5-Di-(t-butyloxycarbonylamino)benzoylamino]ethylamine

Methyl 3,5-di-(t-butyloxycarbonylamino)benzoate (1.98 g, 5.4 mmol) was dissolved in a minimum of ethylene diamine and allowed to react at room temperature for three days. Water was added, and the product (1.84 g, 86% yield) precipitated as a white solid.

3-[2-[3,5-Di-(t-butyloxycarbonylamino]benzoylamino]-ethylaminocarbonyl]]ethylphenol 2-[3,5-Di-(t-butyloxycarbonylamino)benzoylamino]ethylamine (1.85 mg, 0.47 mmol) and N-succinimidyl 4-hydroxyphenylpropionate (Fluka, 105 mg, 0.40 mmol) were dissolved with sonication in 2 ml of MeOH/dimethylformamide (1:1). After 1 hour, 3 ml of water was added. The resulting oil was precipitated from ethyl acetate/hexanes resulting in 136 mg of product (63% yield, homogeneous by TLC, Rf on silica, chloroform:methanol:acetic acid x/y/z=0.xx.

3-[2-[3,5-Diaminobenzoylamino]ethylaminocarbonyl]ethylphenol

3-[2-[3,5-Di-(t-butyloxycarbonylamino)benzoylamino]ethylaminocarbonyl]]ethylphenol was deprotected in x% yield upon dissolving in neat trifluoroacetic acid for 5 minutes, followed by evaporation and precipitation with ether.

3-[2-[3,5-Diisothiocyanatobenzoylamino]ethylaminocarbonyl]ethylphenol

3-[2-[3,5-Diaminobenzoylamino]-ethylaminocarbonyl]ethylphenol was dissolved in a mixture of chloroform (1 mL), dimethylformamide (0.5 mL) and saturated sodium bicarbonate (1 mL). With stirring, thiophosgene (60 uL×u mol) was added. After one hour, the organic layer was washed with water treated with ether. A white precipitate was collected, yield 56 mg (56% yield).

(8-[2-(4-hydroxyphenylpropionylaminoethylaminocarbonyl(benzene-3-isothiocyanato-5-aminothiocarbonylaminoethyl[amino-[carbonyl [methyl[oxyphenyl]]]]]-1,3-dipropylxanthine), XAC (8-[2-Aminoethyl[amino[carbonyl[methyl[oxyphenol]]]]]-1,3-dipropylxanthine, 24 mg, 56 umol) and 3-[2-[3,5-diisothiocyanatobenzoylamino]-ethylaminocarbonyl]ethylphenol (35 mg, 82 umol) were suspended in 1 mL dimethylformamide and sonicated until a solution formed. After one hour, ether was added and a precipitate formed. The product was recrystallized form dimethylformamide/ether to give 39.9 mg (83% yield).

Method F.

N-Hydroxysuccinimidyl 3,5-di-(t-butyloxycarbonylamino)benzoate. 350 mg (1 mmol) of 3,5-di-(t-butyloxycarbonylamino)benzoic acid and 230 mg (1.2 equiv.) of ethyldimethylaminopropylcarbodiimide were placed in 30 ml of $CH_3CN$ and stirred at RT for one hour. To this was added 130 mg (1.2 equiv.) of N-hydroxysuccinimide and the mixture stirred overnight at RT. The mixture was diluted with 150 ml of EtOAc and washed with 100 ml of pH 4 $NaH_2PO_4$. The solvent was removed by rotary evaporator and the residual solid placed on the Chromatotron using $Et_2O$: petroleum ether (1:1) as eluent. The first band was product and 301 mg was collected after removal of solvent.

Preparation of Additional Derivatives

Solubility of Analogs. To 675 uL of pH 7.2 phosphate buffer was added 25 uL of a DMSO solution (approx. 10 mM) of the xanthine to be assayed. This was stirred for one minutes by a vortex mixer then left at room temperature for 2–3 hours. In each case (except where noted) a fine precipitate resulted which was collected by centrifugation at the end of the waiting period. After the dissolution period, a 100 uL aliquot of the supernatant was added to 1.0 mL of methanol and the absorbance measured at 310 nm using an extinction coefficient of 28,180 for calculating the concentration. Each xanthine was assayed 3 times and the concentration represent the averages of these 3 determinations.

Competitive binding assay in rat brain using [$^3$H]PIA, [$^3$H]CGS21680, and [$^3$H]NECA: Inhibition of binding at 1 nM [$^3$H]N$^6$-phenylisopropyladenosine (R-PIA, specific activity 42.5 Ci/mmol) to $A_1$-adenosine receptors in rat cerebral cortex membranes was assayed as described. Inhibition of binding by a range of concentrations of an adenosine derivative was assessed in triplicate in at least three separate experiments. At least seven different concentrations spanning three orders of magnitude, adjusted appropriate for the $IC_{50}$ of each compound were used. $IC_{50}$ values Ci/mmol) or [$^3$H]CGS21680. Inhibition of [$^3$H]NECA binding of to $A_2$-adenosine receptors in rat striatal membranes were measured as described, except that 5 mM theophylline was used to define non-specific binding. $N^6$-Cyclopentyladenosine was present at 50 nM to inhibit binding of the ligand at $A_1$-adenosine receptors. $IC_{50}$ values were converted to $K_i$-values as described.

Irreversible Binding to Rat Brain. For studies of irreversible incorporation, membranes were prepared as described above and then incubated with the indicated (Tables I and II) concentration of ligand for 45 minutes at 37° C. Initial experiments demonstrated that complete incorporation had occurred by sequential resuspension and centrifugations with Buffer A containing 0.02% Chaps. Membranes were then suspended in Buffer A containing $10^{-4}$M 3-isobutyl-1-methylxanthine (IBMX) and incubated at 25° C. for 18 hours with shaking. Membranes were then washed twice with Buffer A, treated with adenosine deaminase as described above, and used in radioligand binding studies as described above.

The long treatment with IBMX was found necessary to remove all of the non-incorporated ligands from membranes. Multiple washes (up to 8) with buffer alone were insufficient to remove all the reversibly bound ligands.

The yields, melting points and elemental analyses for various compounds prepared in accordance with the present invention are provided below in Tables I–IV.

TABLE I

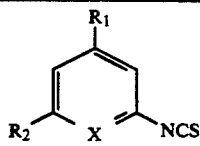

| Cmpd. | % Yield | MP (°C.) | Analysis (C,H,N) Calc./Found |
|---|---|---|---|
| X = N, R1 = H, R2 = NCS | 41 | 48–49 | 43.51; 1.56; 21.74/43.45; 1.61; 21.71 |
| X = C in following: | | | |
| R1 = H, R2 = $CO_2H$ | 96 | 161–162 | 53.62; 2.81; 7.82/53.74; 2.86; 7.87 |
| X = C, R2 = NCS in following | | | |
| R1 = $CO_2Et$ | 96 | 74–75 | 49.99; 3.05; 10.60/49.84; 3.07; 10.50 |
| R1 = $CH_2OH$ | 63 | 79–80 | 48.63; 2.72; 12.60/48.72; 2.76; 12.53 |
| R1 = $CONH_2$ | 87 | 152–153 | 45.95; 2.14; 17.86/46.01; 2.17; 17.82 |
| R1 = NCS | 84 | 64–66 | 43.36; 1,21; 16.85/43.50; 1.30; 16.67 |
| R1 = $CONH(CH_2)_2N(CH_3)_2HCl$ | 49 | 170–172 | 45.54; 4.41; 16.34/45.43; 4.55; 15.96 |
| 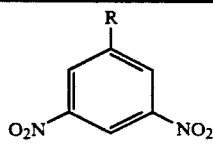 | 51 | 161–161 | 47.57; 1.33; 12.33/47.35; 1.28; 12.31 |
| R1 = $CONH(CH_2)_2NHAc$ | 67 | | |
| R1 = $CONH(CH_2)_2NH$-biotin + $4H_2O$ | 30 | >200 | 49.89; 5.74; 17.16/50.19; 6.02; 16.72 |
| R1 = $NHCSNH(CH_2)_2NHAc$ | 35 | 148–149 | 44.43; 3.73; 19.93/44.53; 3.74; 19.86 |
| R1 = $NHCSNH(CH_2)_2N(CH_3)_2$ | 94 | >250 | 46.27; 4.48; 20.75/ |
| R1 = $NHCSNHCH_2CO_2t$-Bu | 15 | 137–139 | 47.35; 4.24; 14.72/47.33; 4.27; 14.62 |
| R1 = $NHCSNH(CH_2)_2NHCSNH$-fluorescein | 74 | | |
| R1 = $CONH(CH_2)_2NHCSNH$-fluorescein | | | |
| R1 = $CONH(CH_2)_2NHCSNH$-2,2,6,6-tetramethylpiperidinyoxy | | | |
| R1 = $CONH(CH_2)_2SO_3H$ | | | |
| R1 = $NHCSNH(CH_2)_2SO_3H$ | | | |
| R1 = $CONH(CH_2)_2N(CH_3)_3$ | | | |
| R1 = $NHCSNH(CH_2)_2N(CH_3)_3$ | | | |
| R1 = $CONH(CH_2)_2NHCO$-NOS | | | |
| R1 = $CONH(CH_2)_2NHCO$-ASA | | | |
| R1 = $CONH(CH_2)_2NHCO$-NBD | | | |

TABLE II

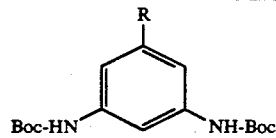

| Cmpd. | % Yield | MP (°C.) | Analysis (C,H,N) Calc./Found |
|---|---|---|---|
| R = $CONH(CH_2)_2N(CH_3)_2 \tfrac{1}{2}H_2O$ | 44 | oil | 45.83; 5.13; 19.44/45.98; 5.03; 19.08 |
| R = $CONH(CH_2)_2N(CH_3)_3I$ | 96 | >250 | 33.98; 4.04; 13.21/34.17; 4.08; 13.25 |
| R = $CONH(CH_2)_2NHAc$ | 62 | 204–205 | 44.60; 4.08; 18.91/44.81; 4.13; 18.81 |

TABLE III

R
Boc-HN — (benzene) — NH-Boc

| Cmpd. | % Yield | MP (°C.) | Analysis (C,H,N) Calc./Found |
|---|---|---|---|
| R = $CO_2H$ | 51.1 | 183–185 | 57.94; 6.86; 7.95/57.77; 6.90; 7.92 |
| R = $CO_2Me$ | 60 | 219–220 | 59.00; 7.15; 7.65/58.81; 7.19; 7.57 |
| R = $CO_2NSu$ | 67 | | 56.12; 6.06; 9.35/56.69; 6.30; 9.20 |
| R = $CONH(CH_2)_2NH_2$ | 87 | 216–217 | 57.85; 7.67; 14.20/57.57; 7.71; 14.24 |
| R = $CONH(CH_2)_2NHCO$-ASA | 85 | >250 | 5621; 5.99; 1765/56.19; 6.02; 1759 |
| R = $CONH(CH_2)_2NHCO$-NOS .25DMF + .5H2O | 83 | | 52.51; 5.72; 18.90/52.26; 5.39; 19.36 |

TABLE III-continued

[Structure: 1,3-bis(Boc-HN)-5-R-benzene]

| Cmpd. | % Yield | MP (°C.) | Analysis (C,H,N) Calc./Found |
|---|---|---|---|
| R = CONH(CH₂)₂NHCSNH-2,2,6,6-tetrapiperidinyoxy | | | |
| R = CONH(CH₂)₂NHCO-Biotin DMF | 65 | 155–158 | 55.39; 7.41; 14.13/55.29; 7.25; 14.03 |
| R = CONH(CH₂)₂NHCO-p-bromomethylphenyl | 84 | | |
| R = CONH(CH₂)₂NHCSNH-fluorescein + 2DMF + 2H₂O | 51 | | 57.19; 6.16; 10.15/57.33; 5.89; 9.75 |

TABLE IV

[Structure: XAC—NHCSNH-pyridyl/phenyl-NCS with R substituent]   X = CH unless noted

| Cmpd. (R =) | % Yield | MP (°C.) | Analysis (C,H,N) Calc./Found |
|---|---|---|---|
| CO₂Et + DMF + .5H₂O | 99 | >250 | 54.23; 5.72; 16.26/54.55; 5.38; 16.05 |
| CH₂OH + H₂O | 97 | >250 | 53.96; 5.28; 16.78/53.74; 5.34; 16.63 |
| X = N, R = H + 0.5H₂O | 72 | >250 | 53.32; 5.11; 19.98/53.45; 5.16; 19.89 |
| CONH₂ + DMF + H₂O | 77 | >250 | 52.63; 5.62; 18.72/52.51; 5.61; 18.55 |
| NCS + 0.5H₂O | 81 | >250 | 52.46; 4.70; 18.35/52.44; 4.75; 18.28 |
| CONH(CH₂)₂N(CH₃)₂ HCl + 2.25H₂O | 79 | >250 | 50.30; 5.90; 17.25/50.09; 5.55; 17.36 |
| CONH(CH₂)₂NHAc | 73 | >250 | |
| NHCSNH(CH₂)₂NHAc | 33 | >250 | |
| NHCSNH(CH₂)₂N(CH₃)₂ | 27 | >250 | |
| [Structure: acetyloxy-3,5-diisothiocyanatobenzoate] | 78 | >250 | |
| NHCSNH(CH₂)₂NHCSNH-fluorescein | | | |
| NHCSNH(CH₂)₂NH-ANB + AcOH + DMF + 2H₂O | 25 | | 48.30; 5.28; 20.96/48.09; 5.14; 20.71 |
| CONH(CH₂)₄NHCO-p-fluoromethylphenyl | | | |
| CONH(CH₂)₂NHCSNH-2,2,6,6-tetrapiperidinyoxy | | | |
| NHCSNHCH₂CO₂t-Bu | | | |
| NHCSNH(CH₂)₂NHCO-ASA | | | |
| CONH(CH₂)₂NHCO-NBD | | | |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. Compounds of the formula

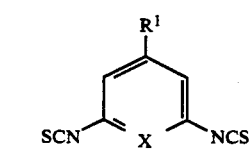

wherein X is CH and R¹ is aminocarbonyl or

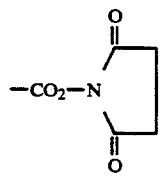

unsubstituted or substituted with: —OH, —COOH, lower ester of COOH, carboxamide, NHCOCH₃, NHCOCH₂Br, halo, dimethylamino, triethylammonium, NHCONH₂, SO₂NH₂, —SO₃H, or a spectroscopic reporter group, coupled through an amido, sulfonamido, amino, thiourea, unsubstituted biotinylamino, or substituted biotinylamino linkage, wherein said biotinylamino linkage is substituted with a spacer chain or;

wherein R¹ is CONH—R₂ or NHCSNH—R₂, wherein R₂ is lower alkyl unsubstituted or substituted with: —OH, —COOH, lower ester of COOH, carboxamide, NHCOCH₃, NHCOCH₂Br, halo, dimethylamino, triethylammonium, NHCONH₂, SO₂NH₂, —SO₃H, or a spectroscopic reporter group, coupled through an amido, sulfonamido, amino, thiourea, unsubstituted biotinylamino, or substituted biotinylamino linkage, wherein said biotinylamino linkage is substituted with a spacer chain.

2. The compounds of claim 1, wherein said spectroscopic reporter group is selected from the group consisting of fluorescent dyes, photoaffinity probes, and spin label probes.

3. The compounds of claim 1, wherein said spacer chain is an ε-aminocaproyl group.

4. The compounds of claim 1, wherein X is CH and R¹ is aminocarbonyl or

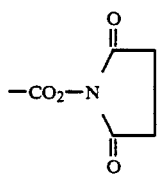

unsubstituted or substituted with: —OH, —COOH, lower ester of COOH, carboxamide, NHCOCH₃, NHCOCH₂Br, halo, dimethylamino, triethylammonium, NHCONH₂, SO₂NH₂, or —SO₃H, or;

wherein R¹ is CONH—R₂ or NHCSNH—R₂, wherein R₂ is lower alkyl unsubstituted or substituted with: —OH, —COOH, lower ester of COOH, carboxamide, NHCOCH₃, NHCOCH₂Br, halo, dimethylamino, triethylammonium, NHCONH₂, SO₂NH₂, or —SO₃H.

5. The compounds of claim 1, wherein R¹ is COHN—R₂ or NHCSNH—R₂, wherein R² is lower alkyl unsubstituted or substituted with: —OH, —COOH, lower ester of COOH, carboxamide, NHCOCH₃, NHCOCH₂Br, halo, dimethylamino, triethylammonium, NHCONH₂, SO₂NH₂, or —SO₃H.

6. A compound of claim 1, wherein R¹ is CONH(CH₂)₂N(CH₃)₂.

7. A compound of claim 1, wherein R¹ is CONH(CH₂)₂NHAc.

8. A compound of claim 1, wherein R¹ is CONH₂.

9. A compound of claim 1, wherein R¹ is NHCSNH(CH₂)₂N(CH₃)₂.

10. A compound of claim 1, wherein R¹ is NHCSNH(CH₂)₂NHAc.

11. A compound of claim 1, wherein R¹ is

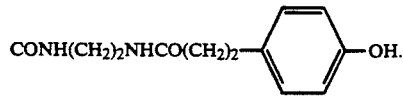

12. A compound of claim 1, wherein R¹ is

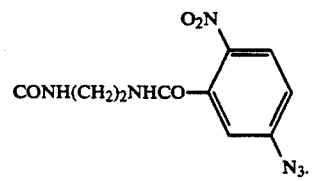

13. A compound of claim 1, wherein R¹ is

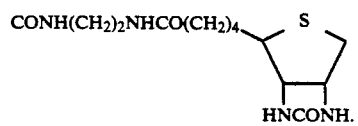

14. A compound of claim 1, wherein R¹ is

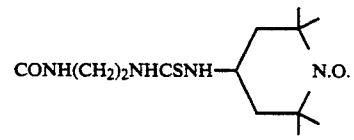

15. A compound of claim 1, wherein R¹ is

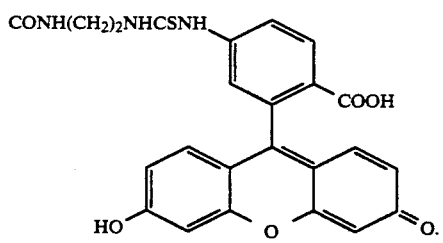

16. The compounds of claim 1, wherein R¹ is COHN—R₂ or NHCSNH—R₂, wherein R² is lower alkyl unsubstituted or substituted with: —OH, —COOH, lower ester of COOH, carboxamide, NHCOCH₃, NHCOCH₂Br, halo, dimethylamino, triethylammonium, NHCONH₂, SO₂NH₂, —SO₃H, or a spectroscopic reporter group, coupled through an amido, sulfonamido, amino, thiourea, unsubstituted biotinylamino, or substituted biotinylamino linkage, wherein said biotinylamino linkage is substituted with a spacer chain.

17. The compounds of claim 16, wherein said spectroscopic reporter group is selected from the group consisting of fluorescent dyes, photoaffinity probes, and spin label probes.

18. The compounds of claim 16, wherein said spacer chain is an ε-aminocaproyl group.

* * * * *